(12) United States Patent
Sakai et al.

(10) Patent No.: US 7,238,822 B2
(45) Date of Patent: Jul. 3, 2007

(54) RUTHENIUM COMPOUND AND PROCESS FOR PRODUCING A METAL RUTHENIUM FILM

(75) Inventors: Tatsuya Sakai, Tokyo (JP); Sachiko Hashimoto, Tokyo (JP); Yasuo Matsuki, Tokyo (JP)

(73) Assignee: JSR Corporation, Tokyo (JP)

( * ) Notice: Subject to any disclaimer, the term of this patent is extended or adjusted under 35 U.S.C. 154(b) by 138 days.

(21) Appl. No.: 10/537,484

(22) PCT Filed: Sep. 17, 2003

(86) PCT No.: PCT/JP03/11848

§ 371 (c)(1),
(2), (4) Date: Jun. 3, 2005

(87) PCT Pub. No.: WO2004/050947

PCT Pub. Date: Jun. 17, 2004

(65) Prior Publication Data

US 2006/0240190 A1   Oct. 26, 2006

(30) Foreign Application Priority Data

Dec. 3, 2002  (JP)  ............... 2002-350951
Jul. 30, 2003  (JP)  ............... 2003-282385

(51) Int. Cl.
   *C07F 17/00*   (2006.01)
   *C23C 16/00*   (2006.01)
(52) U.S. Cl. .................. 556/136; 556/9; 427/252
(58) Field of Classification Search .......... 556/9, 556/136; 427/252
   See application file for complete search history.

(56) References Cited

U.S. PATENT DOCUMENTS 6,063,705 A * 5/2000 Vaartstra .............. 438/681

FOREIGN PATENT DOCUMENTS

| EP | 0 717 451 | 6/1996 |
|---|---|---|
| JP | 6-283438 | 10/1994 |
| JP | 11-35589 | 2/1999 |
| JP | 11-340435 | 12/1999 |
| JP | 2002-69639 | 3/2002 |
| JP | 2002-114795 | 4/2002 |
| JP | 2002-145892 | 5/2002 |
| JP | 2002-161367 | 6/2002 |
| JP | 2002-212112 | 7/2002 |
| JP | 2002-523634 | 7/2002 |
| JP | 2002-231656 | 8/2002 |

\* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

A ruthenium compound from which high-quality film-like metal ruthenium can be obtained and a process for producing a metal ruthenium film from the ruthenium compound by chemical vapor deposition.

The ruthenium compound as a material for chemical vapor deposition is represented by the following formula (1), for example

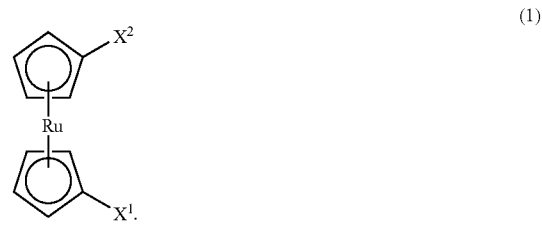

(1)

2 Claims, No Drawings

RUTHENIUM COMPOUND AND PROCESS FOR PRODUCING A METAL RUTHENIUM FILM

FIELD OF THE INVENTION

The present invention relates to a ruthenium compound for chemical vapor deposition and a process for producing a metal ruthenium film from the same by chemical vapor deposition.

DESCRIPTION OF THE PRIOR ART

Heretofore, the capacity of a DRAM (Dynamic Random Access Memory) has been secured by the 3-dimensional structure of each memory cell which comprises a multi-layer film (ON film) consisting of silicon oxide and silicon nitride layers as a dielectric for a capacitor insulator. However, due to recent quick progress in the integration and microfabrication of a DRAM, it has been difficult to secure the capacity of each memory cell with the prior art method.

For further microfabrication, studies on materials such as barium titanate, strontium titanate and PZT having a perovskite crystal structure with a much higher dielectric constant than the ON film are now under way. However, even when the above high-dielectric materials are used in the insulator of a capacitor, a low-dielectric layer may be formed at the interface between an electrode and a dielectric, thereby preventing an increase in the capacity of the capacitor. It is considered that this low-dielectric layer is formed by the movement of an oxygen atom from the dielectric layer to the electrode material. Then, use of platinum and ruthenium as electrode materials which hardly accept oxygen from the dielectric layer and use of ruthenium oxide as an oxide having conductivity are now under investigation. Although a platinum film out of these is difficult to be processed by dry etching, it is known that a metal ruthenium film or ruthenium oxide film can be easily processed by dry etching and can be advantageously used as an electrode for a capacitor comprising a dielectric having a perovskite structure as an insulator.

Although sputtering has been frequently used to form the above metal ruthenium film, studies on chemical vapor deposition are now under way to obtain a finer structure and enable mass-production (refer to, for example, JP-A 11-340435, JP-A 2002-161367, JP-A 2002-212112, JP-A 2002-523634 and JP-A 2002-69639) (the term "JP-A" as used herein means an "unexamined published Japanese patent application").

However, a metal film formed by chemical vapor deposition is inferior in surface morphology that fine crystals are existent sparsely. Therefore, when this film is used as the electrode of a capacitor, leak current is increased by electrostatic focusing. When a very thin electrode film is formed to realize microfabrication, a uniform film cannot be obtained and a film having a defect that metal portions are scattered like islands is formed with the result of deteriorated electric conductivity. When this film is used as the electrode of a capacitor, a large capacitor area cannot be ensured and a capacity required for the operation of the capacitor cannot be obtained.

To solve the above morphology problem, studies on use of bis(dipivaloylmethanate)ruthenium and ruthenocene·bis (alkylcyclopentadienyl)ruthenium as chemical vapor deposition materials are now under way (for example, JP-A 06-283438, JP-A 11-35589 and JP-A 2002-114795).

However, the technology using any one of these chemical vapor deposition materials improves the morphology and the step coverage of a 3-D substrate but involves problems that the conductivity of the obtained film is lower than that of a ruthenium film formed by sputtering and the formed ruthenium film contains a lot of impurities. Therefore, when ruthenium films formed from these raw materials by chemical vapor deposition are used as the electrode of a DRAM, the performance of the DRAM becomes unsatisfactory.

SUMMARY OF THE INVENTION

Problem to Be Solved by the Invention

It is an object of the present invention which has been made in view of the above problem to provide a ruthenium compound for chemical vapor deposition from which high-quality film-like metal ruthenium can be obtained.

It is another object of the present invention to provide a process for producing a metal ruthenium film from the above ruthenium compound.

Other objects and advantages of the present invention will become apparent from the following description.

Means for Solving the Problem

According to the present invention, firstly, the above objects and advantages of the present invention are attained by a ruthenium compound for chemical vapor deposition which is at least one compound selected from the group consisting of a compound represented by the following formula (1):

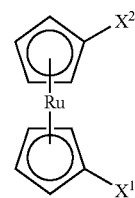

(1)

wherein $X^1$ and $X^2$ are each independently a hydrogen atom, fluorine atom, trifluoromethyl group, pentafluoroethyl group or group represented by the following formula (1)-1:

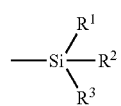

(1)-1 wherein $R^1$, $R^2$ and $R^3$ are each independently a hydrocarbon group having 1 to 10 carbon atoms, with the proviso that $X^1$ and $X^2$ cannot be hydrogen atoms at the same time, a compound represented by the following formula (2):

$$Ru(OCOR^4)_3 \quad (2)$$

wherein $R^4$ is a trifluoromethyl group or hydrocarbon group having 1 to 10 carbon atoms, and three $R^4$'s may be the same or different, a compound represented by the following formula (3):

$$YRu(CO)_3 \qquad (3)$$

wherein Y is a cyclopentadienyl, cyclohexadienyl, cycloheptadienyl, cyclooctadienyl, butadienyl or 2,3-dimethyl-1,3-butadienyl group, and a compound represented by the following formula (4):

$$YRuH_nL_m \qquad (4)$$

wherein Y is as defined in the above formula (3), L is a carbonyl group, methyl group or ethenyl group, n is an integer of 1 to 4, and m is an integer of 0 to 2, with the proviso that n+m is 3 or 4, and two L's may be the same or different when m is 2.

According to the present invention, secondly, the above objects and advantages of the present invention are attained by a process for producing a metal ruthenium film from the ruthenium compound of the present invention by chemical vapor deposition.

The present invention will be described in detail hereinbelow.

The ruthenium compound of the present invention is represented by the above formula (1), (2), (3) or (4).

In the above formula (1), it should be understood that the cyclopentadienyl group having $X^1$ or $X^2$ is coordinated to the ruthenium bond with $\eta^5$-bond.

In the above formula (2), R is a hydrocarbon group having 1 to 10 carbon atoms or trifluoromethyl group, preferably an alkyl group having 1 to 8 carbon atoms or trifluoromethyl group, more preferably methyl group, ethyl group, 2-ethylhexyl group or trifluoromethyl group.

In the above formulas (3) and (4), Y is a cyclopentadienyl group, cyclohexadienyl group, cycloheptadienyl group, cyclooctadienyl group, butadienyl group or 2,3-dimethyl-1,3-butadienyl group. It should be understood that when Y is cyclopentadienyl group, Y is coordinated to the ruthenium atom with $\eta^5$-bond and when Y is a group other than cyclopentadienyl, Y is coordinated to the ruthenium atom with non-conjugated 4-electron bond.

Y is preferably a cyclopentadienyl group, 1,3-cyclohexadienyl group, 1,4-cyclohexadienyl group, 1,3-cyclooctadienyl group, 1,4-cyclooctadienyl group or 2,3-dimethyl-1,3-butadienyl group, preferably cyclopentadienyl group, 1,3-cyclohexadienyl group, 1,4-cyclohexadienyl group or 2,3-dimethyl-1,3-butadienyl group, more preferably cyclopentadienyl group or 2,3-dimethyl-1,3-butadieneyl group. In the above formula (4), L is a carbonyl group, methyl group or ethenyl group, preferably carbonyl group or methyl group, more preferably carbonyl group.

Out of the ruthenium compounds represented by the above formulas (1), (2), (3) and (4), the compounds represented by the above formulas (1), (3) and (4) are preferred, and bis(trifluoromethylcyclopentadienyl)ruthenium, bis(fluorocyclopentadienyl)ruthenium, cyclooctadienyltricarbonyl ruthenium, bis(trimethylsilylcyclopentadienyl)ruthenium, cyclopentadienyl ruthenium tetrahydride, 2,3-dimethyl-1,3-butadienyl ruthenium tetrahydride, cyclopentadienylcarbonyl ruthenium dihydride and 2,3-dimethyl-1,3-butadienylcarbonyl ruthenium dihydride are particularly preferred.

These compounds may be used alone or in combination of two or more as a chemical vapor deposition material(s). It is preferred that one chemical vapor deposition material should be used alone.

The chemical vapor deposition of the present invention is characterized by using the above ruthenium compound.

The chemical vapor deposition of the present invention may be known per se except the above ruthenium compound is used and can be carried out as follows, for example. (1) The ruthenium compound of the present invention is vaporised and (2) the gas is heated to thermally decompose the ruthenium compound as the above chemical vapor deposition material so as to deposit ruthenium on a substrate. The effect of the present invention is not weakened even when the decomposition of the ruthenium compound of the present invention occurs in the above step (1).

The substrate which can be used herein is made of a suitable material such as glass, silicon semiconductor, quartz, metal, metal oxide or synthetic resin but preferably can stand the step temperature for thermally decomposing the ruthenium compound.

In the above step (1), the temperature for vaporization of the ruthenium compound is preferably 50 to 400° C., more preferably 100 to 350° C.

In the above step (2), the temperature for thermally decomposing the ruthenium compound is preferably 80 to 500° C., more preferably 100 to 400° C. This thermal decomposition temperature can be realized by pre-heating the above substrate.

When a compound represented by the above formula (1) is used as the ruthenium compound of the present invention, the thermal decomposition temperature is preferably 150 to 450° C., more preferably 180 to 400° C.

When a compound represented by the above formula (2) is used as the ruthenium compound of the present invention, the thermal decomposition temperature is preferably 200 to 500° C., more preferably 250 to 450° C.

When a compound represented by the above formula (3) is used as the ruthenium compound of the present invention, the thermal decomposition temperature is preferably 80 to 500° C., more preferably 100 to 400° C.

When a compound represented by the above formula (4) is used as the ruthenium compound of the present invention, the thermal decomposition temperature is preferably 100 to 400° C., more preferably 150 to 350° C.

The chemical vapor deposition of the present invention may be carried out in the presence or absence of an inert gas and in the presence or absence of a reducing gas. It may be carried out in the presence of both an inert gas and a reducing gas. Examples of the inert gas include nitrogen, argon and helium. Examples of the reducing gas include hydrogen and ammonia.

The chemical vapor deposition of the present invention may be carried out under pressure, normal pressure or reduced pressure, preferably under normal pressure or reduced pressure, more preferably under a pressure of 15,000 Pa or less.

The thus obtained ruthenium film has high purity and high electric conductivity as obvious from examples which will be described hereinafter and can be advantageously used, for example, as the electrode of a capacitor.

EFFECT OF THE INVENTION

According to the present invention, there are provided a ruthenium compound for chemical vapor deposition by which high-quality film-like metal ruthenium can be obtained and chemical vapor deposition using the same.

BEST MODE FOR CARRYING OUT THE INVENTION

The following examples are provided to further illustrate the present invention.

EXAMPLES

Synthetic Example 1

2.1 g of ruthenium carbonyl ($Ru_3(CO)_{12}$) was weighed and fed to a 200 ml flask whose inside had been substituted by nitrogen and left under reduced pressure at 50° C. for 30 minutes. After the temperature was returned to room temperature, the inside of the flank was substituted by dry nitrogen. 100 ml of well dried toluene and 60 ml of 1,5-cyclooctadiene purified by distillation were added in a nitrogen atmosphere. The obtained solution was heated at 100° C. and stirred for 9 hours. After the end of agitation, the solvent and unreacted cyclooctadiene were distilled off, and the residual viscous solution was let pass through a silica gel column using a hexane developing solvent in a nitrogen atmosphere to collect a dark brown fraction. After the solvent was dried, the mixture was sublimated at 80° C. under a reduced pressure of 133 Pa to obtain 0.8 g of cyclooctadienyl tricarbonyl ruthenium as a yellow needle crystal (yield rate of 31%).

Synthetic Example 2

11 g of trimethylsilyl chloride was dissolved in 30 mol of well dried tetrahydrofuran in a 300 ml flask whose inside had been substituted by nitrogen, and the obtained solution was cooled to −78° C. 100 ml of a tetrahydrofuran solution (2.0 mol/l) of cyclopentadienyl sodium was added dropwise to the above solution in a stream of nitrogen over 1 hour. The solution was stirred at −78° C. for 1 hour and returned to room temperature over 6 hours. A salt precipitated in the mixture solution was removed by filtration in a nitrogen atmosphere, and the residual solution was distilled to obtain 8 g of trimethylsilyl cyclopentadiene.

0.5 g of metal sodium was mixed with a well dried tetrahydrofuran solution in a 300 ml flask whose inside had been substituted by nitrogen, and the resulting solution was cooled to −78° C. A solution of 2.5 g of the above synthesized trimethylsilyl cyclopentadiene dissolved in 30 ml of tetrahydrofuran was added dropwise to the above solution in a stream of nitrogen over 1 hour and further heated to room temperature under agitation for 3 hours to obtain a tetrahydrofuran solution of trimethylsilyl cyclopentadienyl sodium.

Separately, 5 g of dichloro(cyclooctadienyl)ruthenium was dissolved in 200 ml of well dried tetrahydrofuran in a 500 ml flask whose inside had been substituted by nitrogen. This solution was cooled to −78° C., and the above synthesized tetrahydrofuran solution of trimethylsilyl cyclopentadienyl sodium was added dropwise to the above solution in a stream of nitrogen over 1 hour. The resulting solution was stirred at −78° C. for 3 hours and returned to room temperature under agitation over 12 hours. After the solution was let pass through a neutral alumina column in an argon gas atmosphere to be purified and concentrated, it was separated and purified by a neutral alumina column again to obtain 0.9 g of bis(trimethylsilylcyclopentadienyl)ruthenium (yield rate of 13%).

Synthetic Example 3

0.25 g of metal sodium was mixed with well dried tetrahydrofuran in a 100 ml flask whose inside had been substituted by nitrogen and cooled to −78° C. A solution of 1.3 g of trimethylsilyl cyclopentadiene dissolved in 30 ml of tetrahydrofuran was added dropwise to the above solution in a stream of nitrogen over 1 hour and heated to room temperature under agitation over 3 hours to obtain a tetrahydrofuran solution of trimethylsilyl cyclopentadienyl sodium.

Separately, 18 ml of a tetrahydrofuran solution (2.0 mol/l) of cyclopentadienyl sodium was prepared.

Further separately, 5 g of dichloro(1,5-cyclooctadienyl) ruthenium was dissolved in 200 ml of well dried tetrahydrofuran in a 500 ml flask whose inside had been substituted by nitrogen. This solution was cooled to −78° C., and the above tetrahydrofuran solution of trimethylsilyl cyclopentadienyl sodium and the above tetrahydrofuran solution of cyclopentadienyl sodium were added dropwise to the solution at the same time in a stream of nitrogen over 1 hour. The resulting solution was stirred at −78° C. for 3 hours and heated to room temperature under agitation over 12 hours. After the resulting solution was let pass through a neutral alumina column in an argon gas atmosphere to be purified and concentrated, it was separated and purified by a neutral alumina column again to obtain 0.23 g of trimethylsilyl cyclopentadienyl(cyclopentadienyl)ruthenium (yield rate of 4.3%).

Synthetic Example 4

2.1 g of ruthenium carbonyl ($Ru_3(CO)_{12}$) was weighed and fed to a 200 ml flask and left under reduced pressure at 40° C. for 30 minutes. After the flask was returned to room temperature, its inside was substituted by dry nitrogen. 100 ml of well dried toluene and 40 ml of 2,3-dimethyl-1,3-butadiene which was purified by distillation were added in a nitrogen atmosphere. The resulting solution was refluxed at 85° C. and stirred for 9 hours. After the end of agitation, the solvent and unreacted 2,3-dimethyl-1,3-butadiene were removed under reduced pressure, and the residual viscous solution was purified by column chromatography (using silica gel as a filler and hexane as a developing solvent) in a nitrogen atmosphere to collect a dark brown fraction. The solvent was dried and the fraction was purified by sublimation at 130 Pa and 80° C. to obtain 0.6 g of 2,3-dimethyl-1,3-buadienyltricarbonyl ruthenium as a yellow needle crystal (yield rate of 42%).

Synthetic Example 5

2.1 g of ruthenium carbonyl ($Ru_3(CO)_{12}$) was weighed and fed to a 200 ml autoclave whose inside had been substituted by nitrogen and left under reduced pressure at 40° C. for 30 minutes. After the autoclave was returned to room temperature, its inside was substituted by dry nitrogen. 100 ml of well dried toluene and 50 ml of butadiene were added in a nitrogen atmosphere. After the autoclave was closed up, the mixture was heated at 80° C. and stirred for 9 hours. After the end of agitation, the solvent and unreacted butadiene were distilled off, and the residual viscous solution was purified by column chromatography (using silica gel as a filler and hexane as a developing solvent) in a nitrogen atmosphere to collect a dark brown fraction. After the solvent was removed, the fraction was purified by sublimation at 650 Pa and 90° C. to obtain 0.3 g of butadienyltricarbonyl ruthenium as a yellow needle crystal (yield rate of 28%).

Synthetic Example 6

10 g of 2-cyclopenten-1-one was weighed and fed to a 200 ml eggplant-like flask whose inside had been substituted by nitrogen and dissolved in 100 g of toluene. The resulting solution was cooled to −78° C. in a stream of nitrogen, and 0.1 g of trifluoroacetic acid was added. Further, a solution of 22 g of trifluoromethyltrimethylsilane dissolved in 50 ml of toluene was added dropwise to the above solution over 2 hours. After 5 hours of agitation, the obtained reaction mixture was returned to room temperature over 2 hours.

The reaction mixture was purified by distillation and column chromatography (using silica gel as a filler and a mixed solvent of hexane and ethyl acetate as a developing solvent (mixing volume ratio of 8/1)) to obtain 2-trifluoromethyl-2-cyclopenten-1-ol (yield of 7.6 g, yield rate of 42%).

5 g of the above 2-trifluoromethyl-2-cyclopenten-1-ol and 100 ml of dehydrated ethanol were mixed together in another 200 ml flask whose inside had been substituted by nitrogen, the resulting solution was cooled to −10° C. in a stream of nitrogen, and 10 ml of 0.1 N hydrochloric acid was added dropwise over 1 hour. After cooling was stopped, the resulting reaction solution was returned to room temperature under agitation over 3 hours. Thereafter, the reaction solution was heated at 50° C., kept stirred at that temperature for 1 hour and then cooled to room temperature.

The reaction mixture was washed with saturated brine and purified by distillation and column chromatography (using silica gel as a filler and a mixed solvent of hexane and ethyl acetate as a developing solvent (mixing volume ratio of 5/1)) to obtain trifluoromethyl-1,3-cyclopentadiene (yield of 2.6 g, yield rate of 60%).

50 ml of well dried tetrahydrofuran was fed to a 200 ml flask whose inside had been substituted by argon, and 0.5 g of metal sodium was injected into the flask and cooled to −78° C. A solution of 2.5 g of the above synthesized trifluoromethyl-1,3-cyclopentadiene dissolved in 30 ml of tetrahydrofuran was added dropwise over 1 hour and heated to room temperature under agitation over 3 hours to obtain a tetrahydrofuran solution of trifluoromethyl cyclopentadienyl sodium (concentration of 0.62 mol/l).

Separately, 200 ml of well dried tetrahydrofuran was fed to a 500 ml flask whose inside had been substituted by argon, and 5 g of dichloro(cyclooctadienyl)ruthenium was injected into the flask and well mixed with the above tetrahydrofuran to obtain a suspension. This suspension was cooled to −78° C. in a stream of argon, and 15 ml of the above synthesized tetrahydrofuran solution of trifluoromethyl cyclopentadienyl sodium was added dropwise to the suspension over 1 hour. The reaction mixture was further stirred at −78° C. for 3 hours and returned to room temperature under agitation over 12 hours. After the reaction mixture was let pass through a neutral alumina column in a stream of argon to be purified and concentrated, it was purified again by a neutral alumina column to obtain 0.2 g of bis(trifluoromethylcyclopentadienyl)ruthenium (yield rate of 30%).

Synthetic Example 7

10 g of 1,3-cyclopentadienyl-1-ol was weighed and fed to a 200 ml eggplant-like flask whose inside had been substituted by nitrogen and dissolved in 100 g of toluene. The resulting solution was cooled to −78° C. in a stream of nitrogen, and a dilute solution of 25 g of 1,3-dimethyl-2-difluoroimidazolidine diluted with 50 ml of toluene was added dropwise to the above solution over 2 hours.

After 5 hours of agitation, the obtained reaction mixture was returned to room temperature over 2 hours. The reaction mixture was purified by distillation and column chromatography (using silica gel as a filler and a mixed solvent of hexane and ethyl acetate as a developing solvent (mixing volume ratio of 5/1)) to obtain fluorocyclopentadiene (yield of 4.1 g, yield rate of 40%).

50 ml of well dried tetrahydrofuran was fed to a 200 ml flask whose inside had been substituted by argon, 0.5 g of metal sodium was injected into the flask, and the resulting solution was cooled to −78° C. A solution of 2.1 g of the above synthesized fluorocyclopentadiene dissolved in 30 ml of tetrahydrofuran was added dropwise to the above solution over 1 hour and heated at room temperature under agitation for 3 hours to obtain a tetrahydrofuran solution of fluorocyclopentadienyl sodium (concentration of 0.59 mol/l).

Separately, 200 ml of well dried tetrahydrofuran was fed to a 500 ml flask whose inside had been substituted by argon, and 5 g of dichloro(cyclooctadienyl)ruthenium was injected into the flask and well mixed with tetrahydrofuran to obtain a suspension. This suspension was cooled to −78° C. in a stream of argon, and 14 ml of a tetrahydrofuran solution of the above synthesized fluorocyclopentadienyl sodium was added dropwise to the above suspension over 1 hour. The obtained reaction mixture was further stirred at −78° C. for 3 hours and returned to room temperature under agitation over 12 hours. After the reaction mixture was let pass through a neutral alumina column in a stream of argon to be purified and concentrated, it was purified again by a neutral alumina column to obtain 0.4 g of bis(fluorocyclopentadienyl)ruthenium (yield rate of 8.4%).

Synthetic Example 8

9.7 g of trifluoroacetic acid was dissolved in 30 ml of ethanol in a 100 ml eggplant-like flask whose inside had been substituted by argon, and 3.4 g of sodium hydroxide was added to the above solution and stirred at room temperature for 2 hours.

Meanwhile, 5 g of ruthenium chloride trihydrate was dissolved in 100 ml of methanol in another 500 ml three-necked flask whose inside had been substituted by argon. This solution was cooled to 0° C., and the total amount of the above prepared ethanol solution of trifluroacetic acid and sodium hydride was added dropwise to the solution over 1 hour and heated to room temperature under agitation over 3 hours.

This reaction mixture was fed to a 1-liter separatory funnel, 200 ml of ethyl ether was added to the reaction mixture, and the resulting solution was washed with 0.1 N hydrochloric acid twice and then with saturated brine twice. Thereafter, the ether solution was removed under reduced pressure to obtain 3.9 g of ruthenium trifluoroacetate (Ru(OCOC($F_3$)$_3$) (yield rate of 46%).

Synthetic Example 9

12.2 g of 2-ethylhexanoic acid was dissolved in 30 ml of ethanol in a 100 ml eggplant-like flask whose inside had been substituted by argon, and 3.4 g of sodium hydroxide was added to the above solution and stirred at room temperature for 2 hours.

Separately, 5 g of ruthenium chloride trihydrate was dissolved in 100 ml of methanol in another 500 ml three-necked flask whose inside had been substituted by argon. This solution was cooled to 0° C., and the total amount of the above prepared ethanol solution of 2-ethylhexanoic acid and sodium hydroxide was added dropwise to the solution over 1 hour and heated to room temperature under agitation over 3 hours.

This reaction mixture was fed to a 1-liter separatory funnel, 200 ml of ethyl ether was added to the reaction mixture, and the resulting solution was washed with 0.1 N hydrochloric acid twice and then with saturated brine twice. Thereafter, the ether solution was removed under reduced pressure to obtain 5.8 g of ruthenium 2-ethylhexanoate $(Ru(OCOC(C_2H_5)(CH_2)_3CH_3)_3)$ (yield rate of 53%).

Synthetic Example 10

2.1 g of ruthenium carbonyl $(Ru_3(CO)_{12})$ was weighed and fed to a 200 ml flask whose inside had been substituted by argon and left under reduced pressure at 25° C. for 30 minutes. Then, dry argon was introduced into the flask to adjust the inside pressure of the flask to normal pressure, and 100 ml of well dried toluene and 60 ml of cyclopentadiene purified by distillation were added. The resulting solution was heated at 90° C. in a stream of argon and stirred for 4 hours. After the end of agitation, the solvent and unreacted cyclopentadiene were removed under reduced pressure to obtain a red brown paste-like reaction mixture. After this reaction mixture was dissolved in pentane in an argon atmosphere and an undissolved product was separated by filtration, the residual solution was let pass through a neutral alumina column in an argon atmosphere to be purified so as to obtain a yellow fraction. The solvent was then removed under reduced pressure, and the residual solution was purified by sublimation at 133 Pa and 80° C. to obtain 0.15 g of cyclopentadienyltricarbonyl ruthenium as a yellow needle crystal.

A solution of 0.8 g of the above prepared cyclopentadienyltricarbonyl ruthenium dissolved in 50 ml of dry toluene was fed to a 100 ml autoclave whose inside had been substituted by argon. Hydrogen was added to the autoclave at a pressure of 5 MPa and stirred at 120° C. for 5 hours. After the end of agitation, the autoclave was returned to room temperature, hydrogen was discharged, and the reaction mixture was taken out by the pressure of argon. The solvent was removed under reduced pressure, and the reaction mixture was recrystallized by using a mixed solvent of methylene chloride and hexane (mixing volume ratio of 1/20) to obtain 0.3 g of cyclopentadienyl ruthenium tetrahydride (yield rate of 12%).

Synthetic Example 11

2.1 g of ruthenium carbonyl $(Ru_3(CO)_{12})$ was weighed and fed to a 200 ml flask whose inside had been substituted by argon and left under reduced pressure at 25° C. for 30 minutes. Then, dry argon was introduced into the flask to adjust the inside pressure of the flask to normal pressure, and 100 ml of well dried toluene and 30 ml of 2,3-dimethyl-1, 3-butadiene purified by distillation were added. The resulting solution was heated at 90° C., refluxed in a stream of argon and stirred for 4 hours. After the end of agitation, the solvent and unreacted 2,3-dimethyl-1,3-butadiene were removed under reduced pressure to obtain a red brown paste-like reaction mixture. This reaction mixture was dissolved in pentane in an argon atmosphere, and an undissolved product was separated by filtration. This solution was let pass through a neutral alumina column in an argon atmosphere to be purified so as to obtain a yellow fraction. The solvent was then removed under reduced pressure, and the residual solution was purified by sublimation at 133 Pa and 80° C. to obtain 0.13 g of 2,3-dimethyl-1,3-butadienyl-tricarbonyl ruthenium as a yellow needle crystal.

A solution of 0.8 g of the above prepared 2,3-dimethyl-1,3-butadienyltricarbonyl ruthenium dissolved in 50 ml of toluene was fed to a 100 ml autoclave whose inside had been substituted by argon. Hydrogen was added to the autoclave at a pressure of 5 MPa and stirred at 120° C. for 5 hours. After the end of agitation, the autoclave was returned to room temperature, hydrogen was discharged, and the reaction mixture was taken out by the pressure of argon. The solvent was removed under reduced pressure, and the reaction mixture was recrystallized by using a mixed solvent of methylene chloride and hexane (mixing volume ratio of 1/20) to obtain 0.3 g of 2,3-dimethyl-1,3-butadienyl ruthenium tetrahydride.

The resistivity was measured with the RT-80/RG-80 probe resistivity measuring instrument of Napson Co., Ltd. in the following examples. The film thickness was measured with the X' Pert MRD grazing incident X-ray analyzer of Phillips. Co., Ltd. The ESCA spectrum was measured with the JPS80 of JEOL Ltd. The adhesion was evaluated by a cross-cut tape method in accordance with JIS K-5400.

Example 1

0.1 of cyclooctadienyl tricarbonyl ruthenium obtained in Synthetic Example 1 was weighed and fed to a quartz boat-like vessel in an argon gas atmosphere to be set in a quartz reactor. A quartz substrate was placed near the above sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 100 ml/min, the inside pressure of the system was set to 1,333 Pa, and the reactor was heated at 180° C. for 30 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 450 Å. When the ESCA spectrum of this film was measured, a peak attributed to the $RU_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by a 4-terminal method, it was 20 μΩcm. When the adhesion of the formed Ru film to the substrate was evaluated by a cross-cut tape method, the separation of the Ru film from the substrate was not seen at all. Further, this film had a density of 12.2 g/cm³.

Example 2

0.1 g of cyclooctadienyl tricarbonyl ruthenium obtained in Synthetic Example 1 was weighed and fed to a quartz boat-like vessel in an argon gas atmosphere to be set in a quartz reactor. A quartz substrate was placed near the sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 30 ml/min, the inside pressure of the system was set to 80 Pa, and the reactor was heated at 170° C. for 40 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 730 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by the 4-terminal method, it was 17 μΩcm. When the adhesion of the formed Ru film to the substrate was evaluated by the cross-cut tape method, the separation of the Ru film from the substrate was not seen at all. Further, this film had a density of 11.2 g/cm$^3$.

Example 3

0.1 g of bis(trimethylsilylcyclopentadienyl)ruthenium obtained in the above Synthetic Example 2 was weighed and fed to a quartz boat-like vessel in an argon gas atmosphere to be set in a quartz reactor. A quartz substrate was placed near the sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was set to 1,333 Pa, and the reactor was heated at 170° C. for 30 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 350 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by the 4-terminal method, it was 15 μΩcm. When the adhesion of the formed Ru film to the substrate was evaluated by the cross-cut tape method, the separation of the Ru film from the substrate was not seen at all. Further, this film had a density of 11.8 g/cm$^3$.

Example 4

0.1 g of trimethylsilyl cyclopentadienyl(cyclopentadienyl)ruthenium obtained in the above Synthetic Example 3 was weighed and fed to a quartz boat-like vessel in an argon gas atmosphere to be set in a quartz reactor. A quartz substrate was placed near the sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was set to 1,333 Pa, and the reactor was heated at 170° C. for 30 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 380 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by the 4-terminal method, it was 45 μΩcm. When the adhesion of the formed Ru film to the substrate was evaluated by the cross-cut tape method, the separation of the Ru film from the substrate was not seen at all. Further, this film had a density of 11.7 g/cm$^3$.

Example 5

0.1 g of 2,3-dimethyl-1,3-butadienyl tricarbonyl ruthenium obtained in Synthetic Example 4 was weighed and fed to a quartz boat-like vessel in an argon gas atmosphere to be set in a quartz reactor. A quartz substrate was placed near the sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 100 ml/min, the inside pressure of the system was set to 130 Pa, and the reactor was heated at 180° C. for 30 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 450 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by the 4-terminal method, it was 14.3 μΩcm. When the adhesion of the formed Ru film to the substrate was evaluated by the cross-cut tape method, the separation of the Ru film from the substrate was not seen at all. Further, this film had a density of 12.3 g/cm$^3$.

Example 6

0.1 g of butadienyltricarbonyl ruthenium obtained in Synthetic Example 5 was weighed and fed to a quartz boat-like vessel in an argon gas atmosphere to be set in a quartz reactor. A quartz substrate was placed near the sample on a stream side in the reactor, and a nitrogen gas was supplied into the reactor at room temperature and a flow rate of 250 ml/min for 30 minutes. Thereafter, a mixed gas of hydrogen and nitrogen (hydrogen content of 3 vol %) was introduced into the reactor at a flow rate of 100 ml/min, the inside pressure of the system was set to 130 Pa, and the reactor was heated at 120° C. for 30 minutes. Mist was generated from the boat-like vessel, and a deposit was seen on the quartz substrate placed near the sample. After the generation of mist ended, depressurization was stopped, a mixed gas of hydrogen and nitrogen (hydrogen content of 3%) was supplied at 101.3 kPa and a flow rate of 500 ml/min, and the reactor was heated at 350° C. and maintained at that temperature for 1 hour. Then, a film having metallic gloss was obtained on the substrate. The film had a thickness of 450 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. A peak based on carbon was not observed. When the resistivity of this metal ruthenium film was measured by the 4-terminal method, it was 14.9 μΩcm. When the adhesion of the formed Ru film to the substrate was evaluated by the cross-cut tape method, the separation of the Ru film from the substrate was not seen at all. Further, this film had a density of 12.0 g/cm³.

Comparative Example 1

A 600 Å-thick film was obtained in the same manner as in Example 3 except that commercially available bisethylcyclopentadienyl ruthenium was used in place of bistrimethylsilyl cyclopentadienyl ruthenium and the heating temperature of the reactor was set to 300° C. When this film was analyzed by ESCA, a peak attributed to the $Ru_{3d}$ orbit was observed at 280 eV and 284 eV, whereby it was found that the film was a metal ruthenium film. When the resistivity of this metal ruthenium film was measured by the 4-probe method, it was 125 μΩcm. When the adhesion of the formed Ru film to the substrate was evaluated by the cross-cut tape method, all of the 100 squares peeled off from the substrate. Further, this film had a density of 11.2 g/cm³.

Example 7

A quartz boat-like vessel containing 0.1 g of bis(trifluoromethylcyclopentadienyl)ruthenium obtained in Synthetic Example 6 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 30 ml/min, the inside pressure of the system was set to 6,700 Pa, and the reactor was heated at 300° C. Mist was generated from the boat-like vessel, and a deposit was seen on the quartz substrate.

A dry nitrogen gas was introduced to return the inside pressure of the system to normal pressure, and the reactor was heated at 400° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

The film had a thickness of 550 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 23 μΩcm. Further, this film had a density of 12.2 g/cm³.

When the adhesion of the formed Ru film to the substrate was evaluated by the cross-cut tape method, the separation of the Ru film from the substrate was not seen at all.

Example 8

A 540 Å-thick film having metallic gloss was obtained in the same manner as in Example 7 except that a substrate having a silicon thermal oxide film on the surface (manufactured by Electronics & Materials Co., Ltd., trade name of Th—$SiO_2$ series, $SiO_2$ film thickness of 500 Å) was used as the substrate.

When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 20 μΩcm. This film had a density of 12.4 g/cm³.

When the adhesion of the formed Ru film to the substrate was evaluated by the cross-cut tape method, the separation of the Ru film from the substrate was not seen at all.

Example 9

A quartz boat-like vessel containing 0.1 g of bis(fluorocyclopentadienyl) ruthenium obtained in Synthetic Example 7 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was reduced to 1,300 Pa, and the reactor was heated at 200° C. Mist was generated from the boat-like vessel, and a 400 Å-thick deposit was formed on the quartz substrate in 30 minutes at the same time.

A dry nitrogen gas was introduced to return the inside pressure of the system to normal pressure, and the reactor was heated at 400° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

The film had a thickness of 380 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 18 μΩcm. This film had a density of 12.3 g/cm³.

When the adhesion of the formed Ru film to the substrate was evaluated by the cross-cut tape method, the separation of the Ru film from the substrate was not seen at all.

Example 10

A 390 Å-thick film having metallic gloss was obtained in the same manner as in Example 9 except that a substrate having a silicon thermal oxide film on the surface (manufactured by Electronics & Materials Co., Ltd., trade name of Th—$SiO_2$ series, $SiO_2$ film thickness of 500 Å) was used as the substrate.

When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 18 μΩcm. This film had a density of 12.4 g/cm$^3$.

When the adhesion of the formed Ru film to the substrate was evaluated by the cross-cut tape method, the separation of the Ru film from the substrate was not seen at all.

Example 11

A quartz boat-like vessel containing 0.1 g of ruthenium trifluoroacetate obtained in Synthetic Example 8 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was reduced to 1,300 Pa, and the reactor was heated at 250° C. Mist was generated from the boat-like vessel, and a 480 Å-thick deposit was formed on the quartz substrate in 30 minutes at the same time.

A dry nitrogen gas was introduced to return the inside pressure of the system to normal pressure, and the reactor was heated at 500° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

The film had a thickness of 410 Å. When the ESCA spectrum of this film was measured, a peak attributed to the Ru$_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 45 μΩcm. This film had a density of 12.0 g/cm$^3$.

When the adhesion of the formed Ru film to the substrate was evaluated by the cross-cut tape method, the separation of the Ru film from the substrate was not seen at all.

Example 12

A quartz boat-like vessel containing 0.1 g of ruthenium 2-ethylhexanoate obtained in Synthetic Example 9 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 30 ml/min, the inside pressure of the system was reduced to 1,300 Pa, and the reactor was heated at 300° C. Mist was generated from the boat-like vessel, and a 530 Å-thick deposit was formed on the quartz substrate in 30 minutes at the same time.

A dry nitrogen gas was introduced to return the inside pressure of the system to normal pressure, and the reactor was heated at 500° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

The film had a thickness of 400 Å. When the ESCA spectrum of this film was measured, a peak attributed to the Ru$_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 49 μΩcm. This film had a density of 11.9 g/cm$^3$.

When the adhesion of the formed Ru film to the substrate was evaluated by the cross-cut tape method, the separation of the Ru film from the substrate was not seen at all.

Example 13

A quartz boat-like vessel containing 0.1 g of cyclopentadienyl ruthenium tetrahydride obtained in the above Synthetic Example 10 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was reduced to 650 Pa, and the reactor was heated at 300° C. Mist was generated from the boat-like vessel, and a 580 Å-thick deposit was formed on the quartz substrate in 30 minutes at the same time.

A dry nitrogen gas was introduced to return the inside pressure of the system to normal pressure, and the reactor was heated at 350° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

The film had a thickness of 500 Å. When the ESCA spectrum of this film was measured, a peak attributed to the Ru$_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 17 μΩcm. This film had a density of 12.6 g/cm$^3$.

When the adhesion of the formed Ru film to the substrate was evaluated by the cross-cut tape method, the separation of the Ru film from the substrate was not seen at all.

Example 14

A quartz boat-like vessel containing 0.1 g of cyclopentadienyl ruthenium tetrahydride obtained in the above Synthetic Example 10 and a quartz substrate were set in a quartz cylindrical reactor. A nitrogen gas was supplied into the reactor from the quartz boat-like vessel side at room temperature and a flow rate of 250 ml/min for 30 minutes. Thereafter, a nitrogen gas was introduced into the reactor at a flow rate of 50 ml/min, the inside pressure of the system was reduced to 650 Pa, and the reactor was heated at 150° C. Mist was generated from the boat-like vessel, and a 460 Å-thick deposit was formed on the quartz substrate in 30 minutes at the same time.

A dry nitrogen gas was introduced to return the inside pressure of the system to normal pressure, and the reactor was heated at 400° C. and maintained at that temperature for 1 hour while a nitrogen gas was supplied at 101.3 kPa and a flow rate of 500 ml/min. Then, a film having metallic gloss was obtained on the substrate.

The film had a thickness of 380 Å. When the ESCA spectrum of this film was measured, a peak attributed to the Ru$_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 18.1 μΩcm. This film had a density of 12.1 g/cm³.

When the adhesion of the formed Ru film to the substrate was evaluated by the cross-cut tape method, the separation of the Ru film from the substrate was not seen at all.

Example 15

A quartz boat-like vessel containing 0.1 g of 2,3-dimethyl-1,3-butadienyl ruthenium tetrahydride obtained in the above Synthetic Example 11 and a quartz substrate were set in a quartz cylindrical reactor. A nitrogen gas was supplied into the reactor from the quartz boat-like vessel side at room temperature and a flow rate of 250 ml/min for 30 minutes. Thereafter, a nitrogen gas was introduced into the reactor at a flow rate of 50 ml/min, the inside pressure of the system was reduced to 650 Pa, and the reactor was heated at 150° C. Mist was generated from the boat-like vessel, and a 490 Å-thick deposit was formed on the quartz substrate in 30 minutes at the same time.

A dry nitrogen gas was introduced to return the inside pressure of the system to normal pressure, and the reactor was heated at 400° C. and maintained at that temperature for 1 hour while a nitrogen gas was supplied at 101.3 kPa and a flow rate of 500 ml/min. Then, a film having metallic gloss was obtained on the substrate.

The film had a thickness of 410 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 13 μΩcm. This film had a density of 12.6 g/cm³.

When the adhesion of the formed Ru film to the substrate was evaluated by the cross-cut tape method, the separation of the Ru film from the substrate was not seen at all.

Example 16

A quartz boat-like vessel containing 0.1 g of 2,3-dimethyl-1,3-butadienyl ruthenium tetrahydride obtained in the above Synthetic Example 11 and a quartz substrate were set in a quartz cylindrical reactor. A nitrogen gas was supplied into the reactor from the quartz boat-like vessel side at room temperature and a flow rate of 250 ml/min for 30 minutes. Thereafter, a mixed gas of hydrogen and nitrogen (hydrogen content of 3 vol %) was introduced into the reactor at a flow rate of 50 ml/min, the inside pressure of the system was reduced to 650 Pa, and the reactor was heated at 180° C. Mist was generated from the boat-like vessel, and a 470 Å-thick deposit was formed on the quartz substrate in 30 minutes at the same time.

A dry nitrogen gas was introduced to return the inside pressure of the system to normal pressure, and the reactor was heated at 350° C. and maintained at that temperature for 1 hour while a mixed gas of hydrogen and nitrogen (hydrogen content of 3 vol %) was supplied at 101.3 kPa and a flow rate of 500 ml/min. Then, a film having metallic gloss was obtained on the substrate.

This film had a thickness of 410 Å. When the ESCA spectrum of this film was measured, a peak attributed to the $Ru_{3d}$ orbit was observed at 280 eV and 284 eV and a peak derived from another element was not observed at all, whereby it was found that this film was a metal ruthenium film. When the resistivity of this metal ruthenium film was measured by the 4-terminal method, it was 15.8 μΩcm. This film had a density of 12.6 g/cm³.

When the adhesion of the formed Ru film to the substrate was evaluated by the cross-cut tape method, the separation of the Ru film from the substrate was not seen at all.

What is claimed is:

1. A ruthenium compound for chemical vapor deposition, comprising at least one compound selected from the group consisting of:

a compound represented by the following formula (1):

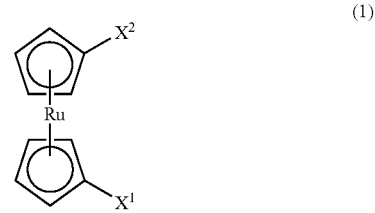

wherein $X^1$ and $X^2$ are each independently a fluorine atom, trifluoromethyl group, pentafluoroethyl group or group represented by the following formula (1)-1:

wherein $R^1$, $R^2$ and $R^3$ are each independently a hydrocarbon group having 1 to 10 carbon atoms; and a compound represented by the following formula (2):

wherein $R^4$ is a trifluoromethyl group or hydrocarbon group having 1 to 10 carbon atoms, and three $R^4$'s may be the same or different.

2. A process for producing a metal ruthenium film comprising applying the ruthenium compound of claim 1 by chemical vapor deposition.

* * * * *